United States Patent
Peuker et al.

(10) Patent No.: US 9,220,578 B2
(45) Date of Patent: Dec. 29, 2015

(54) CAPSULE FOR STORAGE, MIXING AND DISPENSING MATERIALS

(75) Inventors: Marc Peuker, Schondorf (DE); Arno Hohmann, Munich (DE); Helmut Pauser, Diessen (DE)

(73) Assignee: 3M ESPE AG, Seefeld (DE)

( * ) Notice: Subject to any disclaimer, the term of this patent is extended or adjusted under 35 U.S.C. 154(b) by 2035 days.

(21) Appl. No.: 10/598,613

(22) PCT Filed: Mar. 10, 2005

(86) PCT No.: PCT/EP2005/002547
§ 371 (c)(1),
(2), (4) Date: May 29, 2007

(87) PCT Pub. No.: WO2005/094714
PCT Pub. Date: Oct. 13, 2005

(65) Prior Publication Data
US 2007/0272567 A1    Nov. 29, 2007

(30) Foreign Application Priority Data

Mar. 11, 2004   (EP) ................................... 04005800

(51) Int. Cl.
*A61B 19/02* (2006.01)
*A61C 5/06* (2006.01)

(52) U.S. Cl.
CPC ............... *A61C 5/064* (2013.01); *A61C 5/062* (2013.01); *A61C 5/066* (2013.01)

(58) Field of Classification Search
CPC .......................... B65D 81/3266; A61C 19/02
USPC ........... 206/219, 222, 221, 63.5, 368; 433/89, 433/90, 80, 88; 366/602; 604/89, 191, 218; 222/386, 136
See application file for complete search history.

(56) References Cited

U.S. PATENT DOCUMENTS

| | | | | |
|---|---|---|---|---|
| 1,272,283 A | * | 7/1918 | Madden | 222/634 |
| 2,754,590 A | * | 7/1956 | Cohen | 433/90 |
| 2,869,543 A | * | 1/1959 | Ratcliff et al. | 604/90 |
| 3,279,654 A | * | 10/1966 | Pierick | 222/137 |
| 3,348,546 A | * | 10/1967 | Roberts et al. | 604/89 |
| 3,464,412 A | | 9/1969 | Schwartz | 128/218 |
| 3,595,439 A | * | 7/1971 | Newby et al. | 222/80 |
| 3,854,209 A | * | 12/1974 | Franklin et al. | 433/90 |
| 4,017,007 A | * | 4/1977 | Riccio | 222/80 |
| 5,172,807 A | * | 12/1992 | Dragan et al. | 206/219 |
| 5,743,886 A | * | 4/1998 | Lynn et al. | 604/191 |
| 6,386,872 B1 | * | 5/2002 | Mukasa et al. | 433/90 |
| 6,544,233 B1 | * | 4/2003 | Fukui et al. | 604/191 |

(Continued)

FOREIGN PATENT DOCUMENTS

| | | | | |
|---|---|---|---|---|
| CH | 536 237 | 4/1973 | | B65D 81/32 |
| DE | 36 35 574 | 4/1988 | | B65D 81/32 |

(Continued)

*Primary Examiner* — Jacob K Ackun
*Assistant Examiner* — Jenine Pagan (57) ABSTRACT

The present invention relates to a capsule for storage, mixing and dispensing of materials, preferably dental materials like glass ionomer cement. The capsule comprises a capsule body member that provides a main chamber and comprises a dispensing opening; and an applicator member being slideably accommodated in said capsule body member, said applicator member providing an auxiliary chamber. An activator member is slideably accommodated in said applicator member.

15 Claims, 4 Drawing Sheets

(56) References Cited

U.S. PATENT DOCUMENTS

| | | | |
|---|---|---|---|
| 6,554,803 B1 * | 4/2003 | Ashman | 604/218 |
| 6,869,284 B2 * | 3/2005 | Aoyagi et al. | 433/90 |
| 7,131,784 B2 * | 11/2006 | Lee et al. | 401/128 |
| 2001/0053511 A1 * | 12/2001 | Aoyagi et al. | 433/90 |
| 2002/0098462 A1 * | 7/2002 | Kaneko et al. | 433/89 |
| 2003/0136799 A1 | 7/2003 | Peuker et al. | 222/145 |
| 2004/0020796 A1 * | 2/2004 | Cheetham et al. | 206/63.5 |

FOREIGN PATENT DOCUMENTS

| | | | |
|---|---|---|---|
| DE | G 94 00 374.2 | 2/1994 | A61C 5/06 |
| EP | 1 159 931 | 12/2001 | A61C 5/06 |
| FR | 2 286 658 | 4/1976 | A61M 5/18 |
| WO | WO 00/23002 | 4/2000 | A61C 5/06 |

* cited by examiner

CAPSULE FOR STORAGE, MIXING AND DISPENSING MATERIALS

CROSS REFERENCE TO RELATED APPLICATIONS

This application claims the benefit to European Patent Application No. 04005800.0, filed Mar. 11, 2004.

FIELD OF THE INVENTION

The present invention relates to a capsule for storage, mixing and dispensing of materials, preferably dental materials, most preferably glass ionomer cements. In particular, the present invention relates to a capsule for storage, mixing and dispensing materials which preferably consist of a plurality of, i.e., two or more components.

BACKGROUND OF THE INVENTION

Mixing capsules which are filled with the components in separate chambers by the manufacturer are used to produce mixtures of two or more components. The components are brought into communication and mixed with one another by the user, for example by destroying a wall separating the chamber.

Mixing capsules for the production of dental materials which are often mixed from a pulverulent component and a liquid component, the mixing procedure usually talking place in a shaker unit, are known in the dental sector. The completely mixed substance is then dispensed directly onto the working area, for example into a tooth cavity, through a dispensing spout formed integrally on the mixing capsule.

DE-A-36 35 574 discloses a mixing capsule intended for the production of jointing and sealing compounds. In an illustrative embodiment described in said document, an auxiliary chamber which is present in the dispensing piston is delimited, on the side facing the main chamber of the capsule, by a foil and, on the opposite side, by an auxiliary piston which is displaceably arranged in the dispensing piston. In the initial state of the mixing capsule, in addition to the second component, a mixer body is accommodated in the auxiliary chamber, which mixer body initially serves to destroy the foil by means of manual displacement of the auxiliary piston and then assists in the mixing procedure. To allow the reduction in volume which is necessary for displacement of the inner piston together with the mixer body, a gas cushion is provided in the mixing chamber.

In a further embodiment of the known mixing capsule, the mixing body is initially situated in the main chamber. In this case, the auxiliary chamber present in the piston is closed off from the main chamber by means of a cover and on its rear side by a bellows. As a result of manual pressure being applied to the bellows, the cover is pressed away from the piston, so that the two chambers are brought into communication for the purpose of activating the capsule.

In both cases, a dedicated working step which has to be carried out manually is required for activation of the capsule. Furthermore, a gas cushion is required in order to permit the reduction in volume which is required for removal of the cover.

In a multi-component mixing capsule for dental purposes which is known from DE-U-94 00 374, a first component is contained in a mixing chamber and a second, liquid component is contained in a foil bag which is arranged in an auxiliary chamber which is separated from the mixing chamber by a displaceable wall element. A cylindrical mixing body which is present in the mixing chamber is used to displace the wall element at the start of the mixing procedure and thus to compress the foil bag, so that the latter bursts open and releases the liquid component through a liquid passage which is present in the wall element.

US 2003/0136799 discloses a mixing capsule that comprises a cartridge, a dispensing spout and a piston which is displaceably arranged in the cartridge, a sealed main chamber for receiving a first component, an auxiliary chamber which is provided in the piston and receives a second component, at least one freely movable body, and a separating device which separates the auxiliary chamber from the main chamber and through which the body can penetrate. The body is arranged in the main chamber when the separating device closed, and the auxiliary chamber and the body are designed in such a way that, during the dispensing operation, the body can pass into the auxiliary chamber as a displacement body.

SUMMARY OF THE INVENTION

The object of the present invention is to provide an improved capsule for storage, mixing and dispensing of materials that does not require a separate mixing body. This object is solved with the features of the claims.

According to a first aspect, the present invention provides a capsule for storage and mixing and dispensing of materials comprising a capsule body member providing a main chamber, and comprising a dispensing opening, an applicator member being slideably accommodated in said capsule body member, said applicator member providing an auxiliary chamber, and an activator member being slideably accommodated in said applicator member. The main chamber and the auxiliary chamber are selectively connectable for fluid communication between said chambers upon activation of said capsule by said activator member. The main chamber is preferably filled with a powder material, and the auxiliary chamber is preferably filled with a liquid. The applicator member comprises a radially extending through-hole, and the inner wall of the capsule body member comprises a recessed area, said radially extending through-hole and said recessed area forming a channel between said main chamber and said auxiliary chamber upon activation of said capsule.

The activator member is moveably in a longitudinal axis within the applicator member, and the applicator member is moveable within the capsule body member so as to displace a liquid contained in the auxiliary chamber from the auxiliary chamber into the main chamber. In a first step, the activator member is moved so that the liquid contained in the auxiliary chamber is mixed with the substance contained in the main chamber. Upon mixing of these components, the mixture is dispensed through the dispensing opening by a movement of the activator member and the applicator member.

Upon application of a force on the activator member, both the activator member and the applicator member move into the capsule body member due to, e.g., hydraulic transmission. The displacement of the liquid contained in the auxiliary chamber takes place as soon as the radially extending through-hole of the applicator member reaches the recessed area of the capsule body member while moving the two members into the capsule body member.

Preferably, the radially extending through-hole in said applicator member is initially covered by the wall of said capsule body member. More preferably, the radially extending through-hole is located in close proximity to the separation wall separating said auxiliary chamber from said mixing chamber. The through hole can extend perpendicularly to the longitudinal axis of the capsule or more preferably with an angle of less than 90° between the longitudinal axis of the capsule and the axis of the through-hole, whereas the through-hole is inclined to the capsule front side. As an advantage of this design, a complete emptying of the receptacle during mixing is facilitated, thus providing a higher reliability of the mixing ratio.

According to a preferred embodiment, the separation wall of the applicator member comprises a raised area extending towards said activator member.

Furthermore, a raised area, e.g., an annular bulge is provided at the bottom of the capsule body member. The raised area of the body member provides that movement of the applicator member is limited and to maintain a volume that is required as mixing chamber. Once the applicator member contacts the raised area of the body member, all liquid contained in the auxiliary chamber has been channelled into the main chamber, i.e. the mixing chamber.

Preferably, the applicator member comprises a sealing element sealing said through-hole of said applicator member against said body member in a non-activated position of said applicator member. Thus, leakage from the auxiliary chamber to the main chamber is prevented. The sealing element is preferably integrally manufactured with the applicator member or manufactured by two-component injection moulding. Within latter solution the sealing element can be made out of material that is different from the material of the applicator member. An appropriate material combination would be an elastic sealing material and a more rigid plastic for the applicator member, e.g., SEBS (styrene-ethylene-butadiene-styrene) and PP (polypropylene). It is also advantageous to make the sealing material out of a more rigid material relative to a more elastic material for the applicator member. Alternatively, a separate part, e.g. an O-Ring is used.

In addition, said through-hole is preferably covered by a film layer at the outer surface of the applicator member, i.e. the film layer covers the radially outer opening of the through-hole. In the non-activated position of the applicator member, the film layer cannot break even if the pressure within the auxiliary chamber increases since the inner surface of the body member supports the film layer. However, upon activation of the applicator member, i.e. as soon as the through-hole in line with the recessed area, an increasing pressure within the auxiliary chamber causes the film layer to break so that the material contained in the auxiliary chamber can flow into the mixing chamber. Preferably, the film layer is surrounded by the sealing element.

The activator member preferably comprises an activator sealing element for sealing said activator member against said applicator member. The activator sealing element is preferably located adjacent to the front end of the activator member.

It is preferred that additional sealing features are provided separately or in combination at the rear end of the capsule. A first preferred additional sealing feature is formed by a sealing balloon which is attached to the rear end of the applicator member encasing the rear end of the activator member, thus additionally sealing the auxiliary chamber against the exterior of the capsule. The same effect is preferably achieved with a sealing hose that is attached to the rear end of the applicator member and to the rear end of the activator member. Thus, the sealing hose spans the gap between the rear end of the applicator member and the rear end of the activator member. A similar sealing hose is preferably used to provide an additional seal between the body member and the applicator member. This sealing hose spans the gap between the rear end of the body member and the rear end of the applicator member. Alternatively or in addition, another sealing balloon is attached to the rear end of the body member encasing the applicator member and the activator member, thus completely sealing the rear end of the capsule against its exterior. The same effect is achieved with a sealing hose that is attached to the rear end of the body member and to the rear end of the activator member. Thus, the sealing hose spans both the gap between the rear end of the body member and the rear end of the applicator member, and the gap between the rear end of the applicator member and the rear end of the activator member. It should be clear that it is not necessary to provide all of those additional sealing features at the same time. Preferably, at least one of these additional safety features is present.

According to the first aspect of the present invention, all parts within the capsule, i.e. the applicator member and the activator member move smoothly, i.e. are displaceable smoothly. This provides the possibility to activate the capsule only by means of the force that is applied by the holding clamp of the mixing device (that carries the capsule for dispensing material) at the very beginning of the mixing process. There is no manual activation required, i.e. the capsule according to the first aspect of the present invention is a self-activating capsule. It can just be placed in the mixing device which shakes the capsule along its longitudinal axis. This reciprocating motion self-activates the capsule because the applied forces push the activator into the applicator until flow communication between the main chamber and the auxiliary chamber is established. The components are then mixed with each other. This results in a simplified handling and also essential time savings to the dentist.

In order to achieve smooth movement of the parts the sealing members and/or the surfaces facing the seals are preferably coated with a lubricant, e.g. silicon oil. As an option, the lubricant is preferably included in the material of the seal and/or the other parts, e.g. as an additive.

As a further advantage, storage stability is improved due to the use of two-component injection moulded sealing elements. Preferably, the sealing elements are manufactured by a two-component injection moulding process together with the capsule body member, the applicator member and said activator member.

According to the second aspect of the present invention, a capsule for storage, mixing and dispensing of materials comprises a capsule body member providing a main chamber, and comprising a dispensing opening, an applicator member being slideably accommodated in said capsule body member, said applicator member providing an auxiliary chamber and an activator member being slideably accommodated in said applicator member. The main chamber and the auxiliary chamber are selectively connectable for fluid communication between said chambers upon activation of said capsule by said activator member. The main chamber is preferably filled with a powder material, and the auxiliary chamber is preferably filled with a liquid. The activator member comprises an internal channel system extending from the rear end of the activator member to an annular groove remote from the rear end of said activator member.

Preferably, the annular groove of said internal channel system is located adjacent to the front end of the activator member.

Preferably, the internal channel system accommodates a sealing material. According to the capsule of the second aspect of the present invention, the gap between the applicator member and the activator member is hermetically sealed after liquid is filled into the auxiliary chamber of the applicator member, and after assembly of both members due to the sealing member contained in the internal channel system. In particular, the auxiliary chamber is first filled, e.g., with a liquid, and thereafter the activator member is inserted into the applicator member. The outer diameter of the activator member is such that air contained in the auxiliary chamber may escape through a gap between the outer surface of the activator member and the inner surface of the applicator member. This gap is the then closed. Preferably, flowable sealing material is pressed into the channel system of the activator member from the rear end of the activator member towards the radial groove. Since the radial grove exits to the inner surface of the applicator member, the sealing material fills the groove and finally seals the gap between the applicator member and the activator member. At this time, a seal is formed between the applicator member and the activator member thus sealing the auxiliary chamber against the exterior of the capsule. Preferably, the size of the gap between the applicator member and the activator member, the viscosity of the sealing material and the pressure during feeding the sealing material into the internal channel system are adjusted such to avoid that sealing material passes through the gap to the outside of the capsule.

Upon activation of the capsule, i.e., upon pressing the activator member, the seal will loosen from the inner surface of the applicator member. However, the sealing material will still snugly fit into the applicator member so as to prevent that liquid passes through. As soon as a certain level of pressure is reached, the liquid is pressed into the main chamber, i.e. the mixing chamber.

According to a preferred embodiment, the sealing material is a flowable hardenable material, e.g. a hot-melt like ethylene-vinyl-acetate, polyurethane based hotmelts or the like.

Such sealing method of using a flowable sealing material for sealing the applicator member to the activator member may also be used for sealing the connection between cannula and cartridge in order to achieve a tight seal and therefore higher level aging stability of the material stored in the cartridge. In this case the internal channel system for accommodation of the seal material may be arranged within the cartridge and/or the cannula.

It is encompassed by the present invention that the activator member of the second aspect of the present invention is also used in the capsule according to the first aspect of the present invention.

The front end surface of the activator member facing the auxiliary chamber is preferably flat. However, dependent on the liquids to be used, the front end preferably comprises non-flat shapes. For example, in case a liquid is used that forms, when the capsule is held with the dispensing opening down, a convex upper surface or a central peak within the auxiliary chamber, the front end of the activator member preferably comprises a convex or tapering or conical or truncated front end surface. This ensures that the activator member first contacts with its peak the liquid peak thus equalizing the height level of the liquid within the auxiliary chamber, and thus pressing air through the gap between the activator member and the applicator member out of the auxiliary chamber. On the other hand, in case a liquid is used that forms, when the capsule is held with the dispensing opening down, a concave upper surface within the auxiliary chamber so that the lowest level of the liquid is at the centre, the front end of the activator member preferably comprises a reverse truncated or a concave or funnel-shaped front end surface, i.e., with a central recess. This ensures that the activator member first contacts the outer area of the liquid surface. In order to allow air to escape from the little chamber formed by the liquid surface and the front end surface of the activator member, the front end of the activator member comprises a small vent channel that extends from said front end surface to the exterior or environment or surroundings, preferably via said internal channel system of the activator member. Thus, movement of the activator member towards the liquid presses air through the vent channel and the internal channel system out of the auxiliary chamber. The vent channel is dimensioned such that air can escape but is small enough that the sealing material once filled into the internal channel system is prevented from entering the auxiliary chamber through the vent channel.

Preferably, the applicator member wall comprises a through-hole providing a channel between said auxiliary chamber in said applicator member and said main chamber. More preferably, the through-hole is closed by a membrane.

It is preferred according to the second aspect of the present invention that additional sealing features are provided separately or in combination at the rear end of the capsule. A first preferred additional sealing feature is formed by a sealing balloon which is attached to the rear end of the applicator member encasing the rear end of the activator member, thus additionally sealing the auxiliary chamber against the exterior of the capsule. The same effect is preferably achieved with a sealing hose that is attached to the rear end of the applicator member and to the rear end of the activator member. Thus, the sealing hose spans the gap between the rear end of the applicator member and the rear end of the activator member. A similar sealing hose is preferably used to provide an additional seal between the body member and the applicator member. This sealing hose spans the gap between the rear end of the body member and the rear end of the applicator member. Alternatively or in addition, another sealing balloon is attached to the rear end of the body member encasing the applicator member and the activator member, thus completely sealing the rear end of the capsule against its exterior. The same effect is achieved with a sealing hose that is attached to the rear end of the body member and to the rear end of the activator member. Thus, the sealing hose spans both the gap between the rear end of the body member and the rear end of the applicator member, and the gap between the rear end of the applicator member and the rear end of the activator member. It should be clear that it is not necessary to provide all of those additional sealing features at the same time. Preferably, at least one of these additional safety features is present.

The capsule of the first or second aspect may preferably comprise a dispensing cannula connected to the dispensing opening. According to a preferred embodiment, the dispensing cannula is integrally formed with said capsule body member. Alternatively, the cannula is rotatably connected to said capsule body member thus providing a valve.

The materials are preferably dental materials, more preferably glass ionomer cements or resin modified glass ionomer cements.

Preferably, the capsule contains in its main chamber a first, preferably powdery, component of said material to be dispensed, and contains in its auxiliary chamber a second, preferably liquid, component of said material.

According to a third aspect, the present invention provides a kit, comprising at least one of the capsules of any of the first or second aspect of the present invention.

According to a third aspect, the present invention provides the use of the capsules of the first or second aspect for mixing a material of two or more components.

The capsule according to the first or second aspect of the present invention eliminates the need for a separate activation device. This provides a simplified handling and time saving for the dentist. Furthermore, the capsule according to the first or second aspect of the present invention is advantageous because correct activation of the capsule is visible for the dentist which reduces the risk for failures.

The capsule of the present invention does not require conventional burst sachets that require huge burst forces and can therefore be activated without the use of an activator tool. Because the receptacle is formed of a cup like part it can be easily adapted to different volumes by just changing the length of the applicator element. While the maximum volume of burst sachets is limited by various factors that cannot easily be changed within one capsule design, the receptacle of the present capsule allows especially higher volumes to be achieved without major modifications of the capsule.

A further advantage related to the capsule of the first or second aspect of the present invention is that the entire capsule consists of three components only. This optimises manufacturing processes, and reduces manufacturing costs. In particular, the assembly lines for the assembly of the discharge cannula, a cannula holding cap, the sachets and the sachet holding clamp that are conventionally used can be eliminated completely. Furthermore, filling processes (powder and liquid) can be made in line with the assembly of the three parts.

BRIEF DESCRIPTION OF THE DRAWINGS

The present invention will be described in more detail in the following with reference to the drawings in which.

DETAILED DESCRIPTION OF THE PREFERRED EMBODIMENTS

Figure 1:
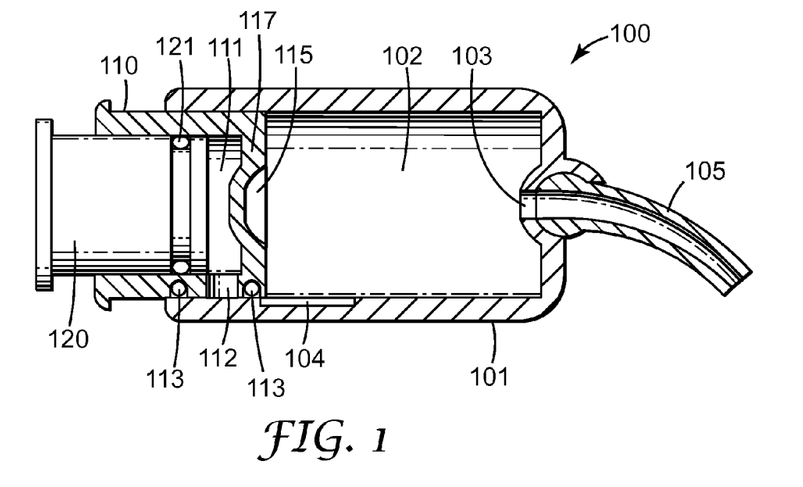
FIG. 1 shows a cross-sectional view of a capsule according to the first aspect of the present invention.

FIG. 1 shows a capsule 100 for storage, mixing and dispensing of materials according to a first aspect of the present invention. The capsule 100 comprises a capsule body member 101 that contains a main chamber 102, i.e. a mixing chamber. Furthermore, the capsule body member 101 comprises a dispensing opening 103. In the embodiment shown in FIG. 1, a dispensing or discharge cannula 105 is connected to the dispensing opening 103. As shown in FIG. 1, the capsule body member 101 is open at one end (in the figure at the left side) in order to receive an applicator member or piston 110. The applicator member or piston 110 is slideably moveably in the capsule body member 101. Movement of the piston to the right reduces the volume of the mixing chamber 102. The applicator piston 110 in turn accommodates an activator member or stamp 120 so that an auxiliary chamber 111 is formed by the applicator member 110 and the activator member 120.

The applicator piston 110 comprises a through-hole 112 that extends radially from the auxiliary chamber 111 to the outer surface of the applicator 110. As illustrated in FIG. 1, the through-hole 112 extends from the auxiliary chamber 111 to the outer circumferential surface of the applicator member 110 and the inner wall of the capsule body 101. As shown in FIG. 1, before activation of the capsule, the radially extending through-hole 112 is covered or closed by the wall of the capsule body member 101. In order to obtain a channel for fluid communication between the main chamber 102 and the auxiliary chamber 111, the capsule body member 101 comprises a recessed area 104, i.e. a bypass area. Upon activation of the capsule, the applicator piston 110 is moved towards the dispensing opening 103. At some point, the through-hole 112 in the applicator piston 110 reaches the bypass 104. At that point, the main chamber 102 and the auxiliary chamber 111 are connected with each other via the bypass 104 and the through-hole 112.

In order to avoid that liquid contained in the auxiliary chamber 111 leaks into the mixing chamber or to the exterior of the capsule, a sealing element 113 is provided to seal the auxiliary chamber against the mixing chamber in the non-activated position of the applicator piston. The sealing element 113 is preferably an O-ring surrounding through-hole 112. Thus, sealing element 113 also seals the auxiliary chamber against the rear end of the capsule body member 101.

In addition, through-hole 112 is preferably covered by a film layer (not shown in FIG. 1) at the outer surface of the applicator piston 110, i.e. the film layer covers the radially outer opening of through-hole 112. In the non-activated position of the applicator piston 110, the film layer cannot break even if the pressure within the auxiliary chamber 111 increases since the inner surface of the capsule body member 101 supports the film layer. However, upon activation of the applicator piston 110, i.e. as soon as the through-hole 112 is in line with the recessed area 104, an increasing pressure within the auxiliary chamber 111 causes the film layer to break so that the material contained in the auxiliary chamber 111 can flow into the mixing chamber 102. Preferably, the film layer is surrounded by the sealing element 113.

A further sealing element 121 is provided at the front end of the activator stamp 120. This activator sealing element is also preferably an O-ring, and prevents that liquid contained in the auxiliary chamber 111 leaks through the space between the inner surface of the applicator piston 110 and the outer surface of the activator stamp 120.

As shown in FIG. 1, the separation wall 117 between the auxiliary chamber and the main chamber preferably comprises a raised area 115, like a bulge.

Figure 2:
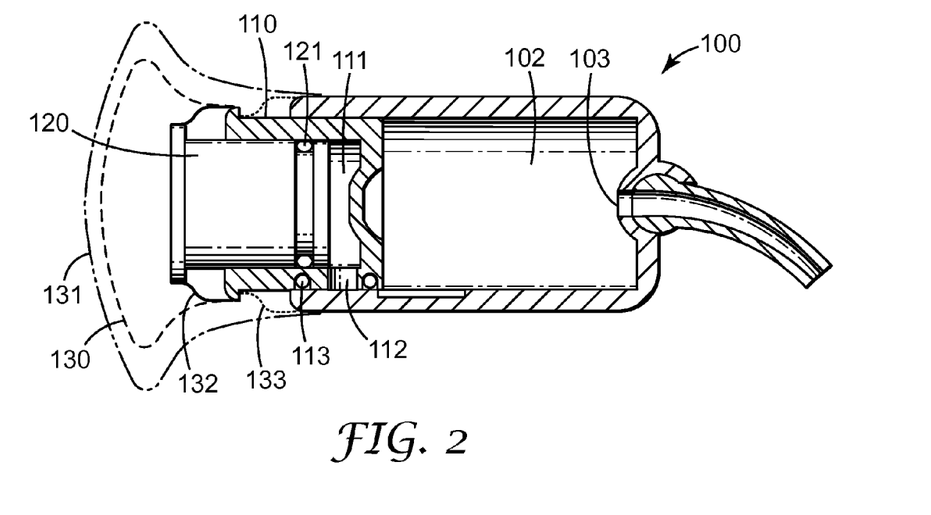
FIG. 2 shows the capsule of FIG. 1 with several additional preferred features.

FIG. 2 shows the capsule 100 of FIG. 1 with further preferred features. In particular, FIG. 2 shows various additional sealing features that are provided separately or in combination. A first preferred additional sealing feature is sealing balloon 130 which is shown in FIG. 2 using dashed line. This sealing balloon 130 is attached to the rear end of the applicator piston 110 and additionally seals the auxiliary chamber 111 against the exterior of the capsule. The same effect can be achieved with a sealing hose 132 that is attached to the rear end of the applicator piston 110 and to the rear end of the activator stamp 120. This sealing hose is shown in FIG. 2 with a solid line. A similar sealing hose 133 is shown in FIG. 2 to provide an additional seal between the capsule body member 101 and the applicator piston 110. The sealing hose 133 spans the gap between the rear end of the capsule body member and the rear end of the applicator piston. Sealing hose 133 is shown in FIG. 2 with a dotted line. Finally, a sealing balloon 131 can be attached to the rear end of the capsule body member 101 encasing the applicator piston 110 and the activator stamp 120 thus completely sealing the rear end of the capsule against its exterior. The same effect is achieved with a sealing hose that is attached to the rear end of the body member 101 and to the rear end of the activator stamp 120. Thus, the sealing hose spans both the gap between the rear end of the body member 101 and the rear end of the applicator piston 110, and the gap between the rear end of the applicator piston 110 and the rear end of the activator stamp 120. It should be clear that it is not necessary to provide all of those additional sealing features, as FIG. 2 may imply. FIG. 2 shows all such safety features at a single capsule just for ease of explanation. Preferably, at least one of those additional safety features is present.

Figure 3:
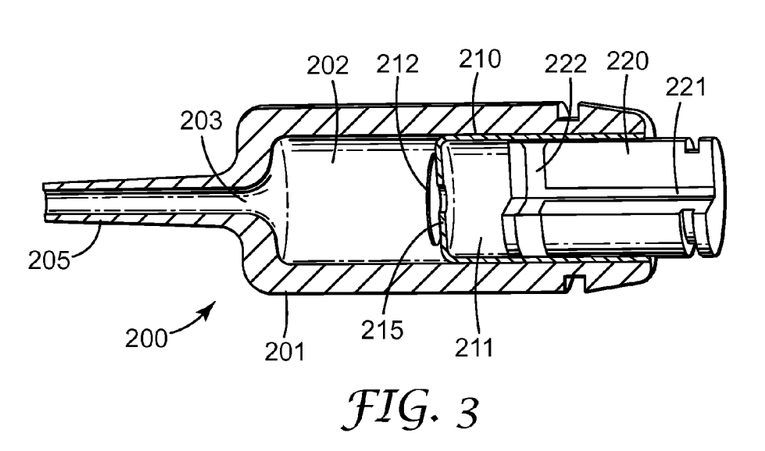
FIG. 3 shows a cross-sectional view of capsule according to the second aspect of the present invention.

FIG. 3 shows a capsule 200 according to a second aspect of the present invention. Capsule 200 comprises a capsule body member 201 with a dispensing opening 203. In the shown embodiment, a discharge cannula 205 is integrally formed with the capsule body member 201. The capsule body member 201 forms a mixing chamber or main chamber 202. Slideably received within the main chamber 202, i.e. within the capsule body member 201 is an applicator member or applicator piston 210. Furthermore, slideably received within the applicator piston 210 is an activator member or activator stamp 220.

The applicator piston 210 comprises a separation wall 215 that separates the auxiliary chamber 211 in the applicator piston 210 from the main chamber 202. As shown in FIG. 3, the separation wall comprises a central through-hole that is covered by a membrane 212 at the side facing the mixing chamber 202.

According to the second aspect of the present invention, the activator stamp 220 comprises an internal channel system 221 that extends from the rear end of the activator stamp 220 towards an area remote from the rear end of the activator stamp 220. In the embodiment shown in FIG. 3, the internal channel system consists of a first central channel reaching from the rear end of the activator stamp to an area adjacent to the front end of the activator stamp 220. In this area, the central channel changes into channels 222 that extend radially and are open towards the inner circumferential surface of the applicator piston 210.

The gap between the applicator piston and the activator stamp 220 is hermetically sealed after liquid is filled into the auxiliary chamber 211 of the applicator member 210, and after assembly of both members due to the sealing member contained in the internal channel system. In particular, the auxiliary chamber 211 is first filled, e.g., with a liquid, and thereafter the activator stamp 220 is inserted into the applicator member 210. The outer diameter of the activator stamp 220 is such that air contained in the auxiliary chamber 211 may escape through a gap between the outer surface of the activator stamp 220 and the inner surface of the applicator member 210. This gap is the then closed. Preferably, flowable sealing material is pressed into the channel system of the activator stamp 220 from the rear end of the activator stamp 220 towards the radial groove. Since the radial grove exits to the inner surface of the applicator member 210, the sealing material fills the groove and finally seals the gap between the applicator member 210 and the activator stamp 220. At this time, a seal is formed between the applicator member 210 and the activator stamp 220 thus sealing the auxiliary chamber 211 against the exterior of the capsule. Preferably, the size of the gap between the applicator member 210 and the activator stamp 220, the viscosity of the sealing material and the pressure during feeding the sealing material into the internal channel system are adjusted such to avoid that sealing material passes through the gap to the outside of the capsule.

The sealing material is preferably a hot melt material. However, other physically hardening, chemically curing materials or combinations thereof could be used as the sealing material. During curing of the sealing material, the seal adheres to the inner surface of the applicator piston 210. However, this seal is separated upon pressing the activator stamp 220. However, the seal still snugly fits into the applicator piston so that any leakage of liquid from the auxiliary chamber through the space between the activator stamp 220 and the applicator piston 210 is prevented. As soon as a certain pressure level is reached, the membrane which seals the through-hole in the applicator piston 210 is broken, and the liquid contained in the auxiliary chamber 211 flows into the mixing chamber 202.

Figure 4:
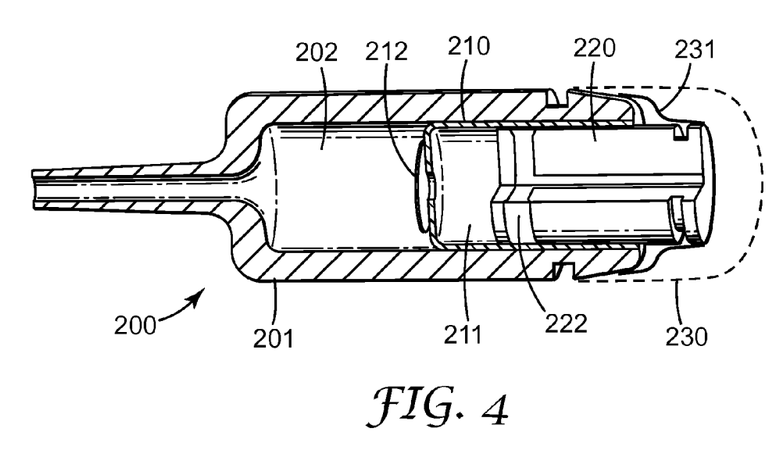
FIG. 4 shows the capsule of FIG. 3 with additional preferred features.

FIG. 4 shows the capsule 200 of FIG. 3 with further preferred features. In particular, FIG. 4 shows various additional sealing features that are provided separately or in combination. A first preferred additional sealing feature is sealing balloon 230 which is shown in FIG. 4 using dashed line. This sealing balloon 230 is attached to the rear end of the body member 201 and additionally seals the main chamber 202 and the auxiliary chamber 211 against the exterior of the capsule. The sealing balloon 230 encases the rear ends of the applicator piston 210 and of the activator stamp 220. The same effect can be achieved with a sealing hose 231 that is attached to the rear end of the body member 201 and to the rear end of the activator stamp 220. This sealing hose 231 is shown in FIG. 4 with solid line. The sealing hose 231 spans the gaps between the rear end of the capsule body member 201 and the rear end of the activator stamp 220. Another preferred additional sealing feature is a sealing balloon (not shown in FIG. 4) which is attached to the rear end of the applicator piston 210 and additionally seals the auxiliary chamber 211 against the exterior of the capsule, like sealing balloon 130 shown in FIG. 2. The same effect can be achieved with a sealing hose (not shown in FIG. 4) that is attached to the rear end of the applicator piston 210 and to the rear end of the activator stamp 220, like sealing hose 132 shown in FIG. 2. A similar sealing hose (not shown in FIG. 4) is preferably present to provide an additional seal between the capsule body member 201 and the applicator piston 210, like sealing hose 133 shown in FIG. 2. Such sealing hose spans the gap between the rear end of the capsule body member 201 and the rear end of the applicator piston 210. It should be clear that it is not necessary to provide all of those additional sealing features, as FIG. 4 may imply. FIG. 4 shows both such safety features at a single capsule just for ease of explanation. Preferably, at least one of these additional safety features is present.

Figure 5:
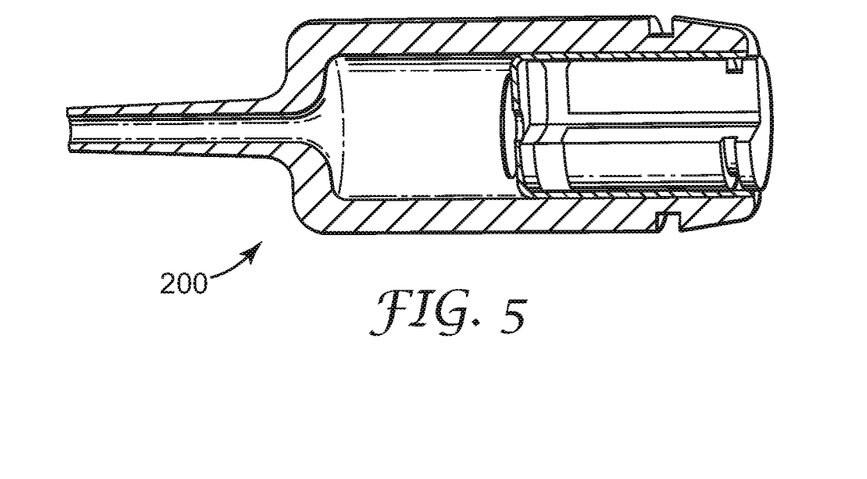
FIG. 5 shows a cross-sectional view of an activated capsule according to the second aspect of the present invention.

The fully activated capsule according to the second aspect of the present invention is shown in FIG. 5.

Figure 6:
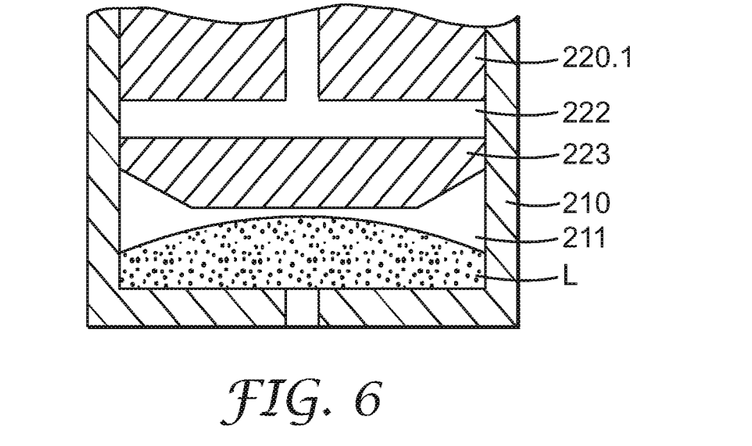
FIG. 6 shows an alternative design of the front end of the activator member of the second aspect of the present invention.

The front end surface of the activator stamp 220 facing the auxiliary chamber 211 is preferably flat. However, dependent on the liquids to be used, the front end preferably comprises non-flat shapes. For example, as shown in FIG. 6, in case a liquid L is used that forms a central peak within the auxiliary chamber 211, the front end 223 of the activator stamp 220.1 is preferably truncated. This ensures that the activator stamp 220.1 first contacts with its peak the liquid peal thus equalizing the height level of the liquid L within the auxiliary chamber 211, and thus pressing air through the gap between the activator stamp 220.1 and the applicator piston 210 out of the auxiliary chamber 211.

Figure 7:
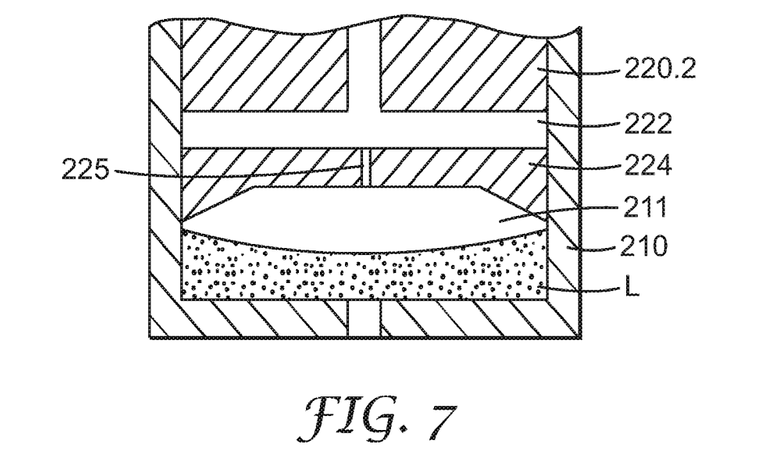
FIG. 7 shows a further alternative design of the front end of the activator member of the second aspect of the present invention.

On the other hand, as shown in FIG. 7, in case a liquid L is used that forms a concave surface, i.e., a meniscus, within the auxiliary chamber 211 so that the lowest level of the liquid is at its centre, the front end 223 of the activator stamp 220.2 preferably comprises a reverse truncated shape, i.e., with a central recess. This ensures that the activator stamp 220.2 first contacts the outer area of the liquid surface. In order to allow air to escape from the small chamber formed by the liquid surface and the front end surface of the activator stamp 220.2, the front end of the activator stamp 220.2 comprises a small vent channel 225 that is connected to the exterior or environment or surroundings via the internal channel system 222 of the activator stamp 220.2. Thus, movement of the activator stamp 220.2 towards the liquid presses air through the vent channel 225 and the internal channel system 222 out off the auxiliary chamber 211. The vent channel 225 is dimensioned such that air can escape but is small enough that the sealing material once filled into the internal channel system 222 is prevented from entering the auxiliary chamber 211 through the vent channel 225.

LIST OF REFERENCE SIGNS 100 capsule
101 capsule body member
102 main chamber
103 dispensing opening
104 recessed area
105 discharge cannula
110 applicator piston
111 auxiliary chamber
112 through-hole
113 sealing element
115 raised area
120 activator stamp
121 sealing element
130 sealing balloon
131 sealing balloon
132 sealing hose
133 sealing hose
200 capsule
201 capsule body member
202 main chamber
203 dispensing opening
205 discharge cannula
210 applicator piston
211 auxiliary chamber
212 membrane
220 activator stamp
220.1 activator stamp
220.2 activator stamp
221 internal channel system
222 radial channels
223 activator stamp front end
224 activator stamp front end
225 vent channel
230 sealing balloon
231 sealing hose
L liquid

The invention claimed is:

1. Capsule for storage and mixing and dispensing of dental material comprising:
a capsule body member providing a main chamber, and comprising a dispensing opening, wherein the inner wall of the capsule body member comprises a recessed area;
an applicator member adapted for slideable accommodation in said capsule body member, said applicator member providing an auxiliary chamber, and wherein said applicator member comprises a through-hole extending from the auxiliary chamber to the outer circumferential surface of the applicator member and the inner wall of the capsule body; and
an activator member being slideably accommodated in said applicator member;
said through-hole and said recessed area forming a channel between said main chamber and said auxiliary chamber upon activation of said capsule due to movement of both said activator member and said applicator member further into the main chamber towards said dispensing opening, where the movement of said applicator member is due to force applied to the activator member through a liquid in the auxiliary chamber to the applicator member, with the activator member moving towards the through-hole of the applicator member upon the channel forming between said main chamber and said auxiliary chamber.

2. The capsule of claim 1, wherein said through-hole in said applicator member is initially covered by the wall of said capsule body member.

3. The capsule of claim 1, wherein said through-hole is located in close proximity to a separation wall of said applicator member separating said auxiliary chamber from said mixing chamber.

4. The capsule of claim 1, wherein said through-hole extends essentially perpendicularly to the longitudinal axis of said applicator member.

5. The capsule of claim 1, wherein said through-hole extends essentially at an angle smaller than 90° to the longitudinal axis of said applicator member.

6. The capsule of claim 3, wherein said separation wall comprises a raised area extending towards said activator member.

7. The capsule of claim 6, wherein said raised area comprises an annular bulge.

8. The capsule of claim 1, wherein said applicator member comprises a sealing element sealing said through-hole of said applicator member against said recessed area of said body member and against the exterior of said capsule.

9. The capsule of claim 1, said activator member comprising an activator sealing element for sealing said activator member against said applicator member.

10. The capsule of claim 8, wherein said sealing elements are manufactured by a two-component injection moulding process together with the capsule body member, the applicator member and said activator member.

11. The capsule of claim 1, further comprising a dispensing cannula connected to said dispensing opening.

12. The capsule of claim 11, wherein the dispensing cannula is integrally formed with said capsule body member.

13. The capsule of claim 11, wherein said cannula is rotatably connected to said capsule body member thus providing a valve.

14. The capsule of claim 1, wherein the capsule contains components of a glass ionomer cement or a resin modified glass ionomer cement.

15. The capsule of claim 1, wherein said main chamber contains a first component of a dental material, and said auxiliary chamber contains a second component of a dental material.

* * * * *